United States Patent
De Clermont Gallerande et al.

(10) Patent No.: US 11,246,811 B2
(45) Date of Patent: Feb. 15, 2022

(54) SOLID COSMETIC COMPOSITION WITH A MOISTURIZING EFFECT

(71) Applicant: CHANEL PARFUMS BEAUTE, Neuilly sur Seine (FR)

(72) Inventors: Hélène De Clermont Gallerande, Vincennes (FR); Aurélie Bonnefoy, Saint-Ouen l'Aumone (FR)

(73) Assignee: CHANEL PARFUMS BEAUTE, Neuilly sur Seine (FR)

( * ) Notice: Subject to any disclaimer, the term of this patent is extended or adjusted under 35 U.S.C. 154(b) by 78 days.

(21) Appl. No.: 16/472,156

(22) PCT Filed: Dec. 20, 2016

(86) PCT No.: PCT/IB2016/001970
§ 371 (c)(1),
(2) Date: Jun. 20, 2019

(87) PCT Pub. No.: WO2018/115918
PCT Pub. Date: Jun. 28, 2018

(65) Prior Publication Data
US 2020/0016048 A1 Jan. 16, 2020

(51) Int. Cl.
*A61K 8/06* (2006.01)
*A61K 8/55* (2006.01)
*A61K 8/92* (2006.01)
*A61Q 1/06* (2006.01)
*A61K 8/02* (2006.01)
*A61K 8/34* (2006.01)
*A61K 8/44* (2006.01)

(52) U.S. Cl.
CPC ............ *A61K 8/064* (2013.01); *A61K 8/0229* (2013.01); *A61K 8/345* (2013.01); *A61K 8/44* (2013.01); *A61K 8/55* (2013.01); *A61K 8/553* (2013.01); *A61K 8/922* (2013.01); *A61K 8/927* (2013.01); *A61Q 1/06* (2013.01); *A61K 8/925* (2013.01); *A61K 2800/59* (2013.01)

(58) Field of Classification Search
None
See application file for complete search history.

(56) References Cited

U.S. PATENT DOCUMENTS

| | | | | |
|---|---|---|---|---|
| 4,536,519 A | * | 8/1985 | Suzuki | A61K 8/06 514/143 |
| 5,085,856 A | * | 2/1992 | Dunphy | A61K 8/375 424/64 |
| 6,264,933 B1 | | 7/2001 | Bodelin et al. | |
| 2005/0191328 A1 | | 9/2005 | Taniguchi | |

FOREIGN PATENT DOCUMENTS

| | | |
|---|---|---|
| EP | 0 542 669 A1 | 5/1993 |
| EP | 0 787 730 A1 | 8/1997 |
| EP | 0 787 731 A2 | 8/1997 |
| FR | 2 933 865 A1 | 1/2010 |
| JP | 2002-500672 A | 1/2002 |
| JP | 2013-177367 | 9/2013 |
| JP | 2015-189696 | 11/2015 |
| JP | 2016-088872 | 5/2016 |
| KR | 10-2000-0062213 A | 10/2000 |
| KR | 10-2006-0116228 A | 11/2006 |
| WO | 96/08537 A1 | 3/1996 |
| WO | 98/53793 A1 | 12/1998 |
| WO | WO 00/47182 | 8/2000 |
| WO | WO-0047182 A1 * | 8/2000 ............ A61Q 15/00 |

OTHER PUBLICATIONS

International Search Report, PCT/IB2016/001970, dated Apr. 3, 2017.
Watanabe et al., "α-gel prepared in sodium methyl stearoyl taurate/behenyl alcohol/water system-characterization of structural changes with water concentration," Journal of Oleo Science, vol. 61, 2012, pp. 29-34.

* cited by examiner

*Primary Examiner* — H. Sarah Park
(74) *Attorney, Agent, or Firm* — Nixon & Vanderhye (57) ABSTRACT

Disclosed is a cosmetic composition in the form of a solid water-in-oil emulsion, for example a lipstick, a lip balm, a foundation or a concealer. It also relates to a cosmetic method for caring for or making up the lips or the skin, including the topical application to the lips or the skin of this composition.

13 Claims, 1 Drawing Sheet

SOLID COSMETIC COMPOSITION WITH A MOISTURIZING EFFECT

BACKGROUND OF THE INVENTION

Field of the Invention

The present invention relates to a cosmetic composition in the form of a solid water-in-oil emulsion, for example a lipstick, a lip balm, a foundation or a concealer. It also relates to a cosmetic method for caring for or making up the lips or the skin, comprising the topical application of this composition to the lips or the skin.

Description of the Related Art

Solid cosmetic compositions are usually used for stick type cosmetics such as lipsticks, lip balms, concealers and foundations. Waxes are generally introduced in stick type cosmetics so as to obtain a product that can be cast in the desired form when heated and that solidifies at room temperature.

Solid water-in-oil emulsions comprising humectants are particularly interesting because they provide a moisturizing effect on the skin or the lips. However, to obtain a satisfying moisturizing effect, it is necessary to include substantial amounts of water and humectants which is detrimental to the stability of the cosmetic composition. Moreover, it is difficult to formulate a solid water-in-oil emulsion that provides a long-lasting moisturizing effect.

The Applicant has found that substantial amounts of water and humectants can be introduced in solid water-in-oil emulsions by forming lamellar phases, preferably alpha gels, therein. Solid water-in-oil emulsions comprising lamellar phases, especially alpha gels, can be obtained with the specific combination of a non-ionic alkyl phosphate and a base. Indeed, the water and the humectant are entrapped between the lipid bilayers of the lamellar phases and are progressively released on the skin or the lips over a long period of time after application of the cosmetic composition.

The present invention therefore provides a cosmetic composition in the form of a solid water-in-oil emulsion that exhibits a long lasting moisturizing effect when it is applied on the lips or the skin.

SUMMARY OF THE INVENTION

A first object of the present invention is a cosmetic composition in the form of a solid water-in-oil emulsion comprising:
  a non-ionic alkyl phosphate;
  a base;
  a humectant;
  at least 8% by weight, preferably at least 10% by weight, of water based on the weight of the composition;
  a structuring agent;
  an oil.

A second object of the present invention is a cosmetic composition in the form of a solid water-in-oil emulsion comprising lamellar phases, preferably alpha gels.

A third object of the present invention is a cosmetic composition in the form of a solid water-in-oil emulsion comprising:
  a non-ionic alkyl phosphate;
  a base;
  a humectant;
  from 4% to less than 8% by weight of water based on the weight of the composition;
  a structuring agent;
  an oil;
  wherein the structuring agent does not comprise a wax selected from carnauba wax, synthetic wax, polyethylene wax or ozokerite.

Another object of the present invention is a lipstick, lip balm, foundation or concealer comprising a cosmetic composition according to the invention.

Yet another object of the present invention is a cosmetic method for caring for or making up the lips or the skin, comprising the topical application to the lips or the skin of a cosmetic composition according to the invention.

Solid Water-in-Oil Emulsion

The cosmetic composition of the present invention is in the form of a solid water-in-oil emulsion.

A water-in-oil emulsion comprises an aqueous phase dispersed in a continuous oily phase.

The term "solid water-in-oil emulsion" means a water-in-oil emulsion that does not flow under its own weight at a temperature range at which cosmetics are generally used, namely 0° C. to 50° C.

The cosmetic composition of the invention is however liquid, i.e. it flows under its own weight, when heated at a temperature range of above 50° C. to 110° C. Indeed, the cosmetic composition of the present invention is preferably in the form of a stick or a cast product in a dish that can, for example, be obtained by heating the composition and casting it in a suitable container.

According to a preferred embodiment, the cosmetic composition of the present invention is in the form of a solid water-in-oil emulsion comprising lamellar phases, preferably alpha gels.

The term "lamellar phases" means a plurality of stacked lipid bilayers separated by an aqueous layer.

The term "alpha gels", means lamellar phases that are ordered into a «L beta» and/or «L beta'» crystal form.

The presence of lamellar phases and alpha gels in the cosmetic composition of the invention may, for example, be determined by electronic microscopy and/or X-Ray diffraction (XRD) analysis. Indeed, alpha gels exhibit characteristic maltese cross-shaped inclusions in electronic microscopy and well-defined Wide Angle X-Ray Scattering (WAXS) peaks in DRX. WAXS is an X-ray-diffraction technique that is often used to determine the crystalline structure of polymers. This technique specifically refers to the analysis of Bragg peaks scattered to wide angles caused by sub-nanometer-sized structures. Watanabe et al. *Journal of Oleo Science*, 2012 61, (1), p.29-32 provides details on the characterization of alpha gels by WAXS.

A cosmetic composition comprising lamellar phases, preferably alpha gels, can, in particular, be obtained with a specific emulsifying system comprising a non-ionic alkyl phosphate, such as cetyl phosphate, and a base, such as a basic amino acid, preferably arginine.

Non-Ionic Alkyl Phosphate

The cosmetic composition of the present invention comprises a non-ionic alkyl phosphate or mixtures thereof.

The term "alkyl phosphate" means a compound of formula $R-OPO_3H_2$ wherein R is an alkyl group, preferably an alkyl group comprising 12 to 22 carbon atoms, more preferably an alkyl group comprising 16 to 18 carbon atoms.

The term "non-ionic alkyl phosphate" means an alkyl phosphate that is in the form of a phosphoric acid. As such, the phosphoric acid group of the alkyl phosphate is not neutralized by forming a salt with a cationic counterion, such as for example an ammonium, sodium or potassium counterion.

Examples of suitable non-ionic alkyl phosphates include lauryl phosphate, myristyl phosphate, cetyl phosphate, stearyl phosphate, eicosyl phosphate, behenyl phosphate, and mixtures thereof.

According to a particularly preferred embodiment, the non-ionic alkyl phosphate is cetyl phosphate.

Suitable examples of cetyl phosphate that can be used in the composition of the invention include Purephos® alpha available from Nikkol, Amphisol® A available from DSM, Crodafos® MCA-PA available from Croda or Hostaphat® CC 100 available from Clariant International Ltd.

Advantageously, the non-ionic alkyl phosphate, preferably the cetyl phosphate, is neutralized by the base comprised in the cosmetic composition.

The cosmetic composition of the invention may, in particular, comprise 0.5 to 5% by weight, preferably 1 to 2.5% by weight, of non-ionic alkyl phosphate based on the weight of the composition.

Base

The cosmetic composition of the present invention comprises a base or mixtures thereof.

Examples of suitable bases include conventional bases in chemistry such as ammonia.

The base may also be an amino-alcohol such as diethanolamine (DEA), triethanolamine (TEA), triisopropanolamine (TIPA), 2-amino-2-methylpropanol (AMP), 2-amino-2-methyl-1,3-propanediol (AMPD) or 2-amino-2-(hydroxymethyl)-1,3-propanediol (THAM).

The base may also be a basic amino acid.

Preferably, the base is a basic amino acid.

The term "basic amino acid" means an amino acid that has a basic side chain at neutral pH.

Examples of suitable basic amino acid include arginine, histidine, lysine and mixtures thereof.

The basic amino acid can be in the L or D isomer form, preferably in the L isomer form.

According to a particularly preferred embodiment, the basic amino acid is arginine, preferably L-arginine.

The weight ratio of the non-ionic alkyl phosphate to the base is 1/1 to 3/1, preferably 1.5/1 to 2.5/1, more preferably approximately 2/1.

The cosmetic composition of the invention may, in particular, comprise 0.2 to 2.5% by weight, preferably 0.5 to 1% by weight, of base based on the weight of the composition.

Humectant

The cosmetic composition of the present invention comprises a humectant or mixtures thereof.

The term "humectant" means a compound comprising at least two hydrophilic groups, i.e. groups that form hydrogen bonds with molecules of water, such as, for example, hydroxyl, amine and/or carboxyl groups.

Examples of suitable humectants include glycerol; glycols, such as propylene glycol, butylene glycol and hexylene glycol; sugar alcohols or sugar polyols, such as sorbitol, xylitol and maltitol; polymeric polyols, such as polydextrose; alpha-hydroxy acids such as lactic acid; hyaluronic acid; urea; pyroglutamic acid (PCA); and mixtures thereof.

According to a particularly preferred embodiment, the humectant is selected from glycerol, a glycol and mixtures thereof.

The cosmetic composition of the invention may, in particular, comprise 1 to 30% by weight, preferably 5 to 20% by weight, more preferably 8 to 15% by weight, of humectant based on the weight of the composition.

Water

The cosmetic composition of the present invention comprises water.

Preferably, the cosmetic composition of the present invention comprises demineralized water.

According to a first embodiment of the present invention, the composition comprises at least 8% by weight, preferably at least 10% by weight, of water based on the weight of the composition. In particular, the amount of water may be up to 30% by weight, preferably up to 20% by weight, even more preferably up to 12% by weight of water. In the composition of said first embodiment, the nature of the wax that can be used as a structuring agent is not particularly limited.

According to a second embodiment of the present invention, the composition comprises from 4% to less than 8% by weight of water based on the weight of the composition. According to said second embodiment, the cosmetic composition does not comprise a wax selected from carnauba wax, synthetic wax (Sasol wax), polyethylene wax (P400) or ozokerite.

Structuring Agent

The cosmetic composition of the present invention comprises a structuring agent or mixtures thereof.

The term "structuring agent" means an agent that is capable of structuring the oily phase of the composition.

According to a preferred embodiment, the structuring agent of the composition of the invention is a wax, an oily gellant or mixtures thereof.

The term "wax" means a fatty substance with a reversible liquid/solid state change, having a melting temperature above 30° C. and generally less than 110° C., which is liquid under the conditions for preparing the composition and has an anisotropic crystalline organization in the solid state.

The term "oily gellant" means a substance that is able to solidify or gelatinize the oil introduced in the composition of the invention.

Preferably, the structuring agent of the cosmetic composition of the invention is a mixture of at least two waxes, more preferably a mixture of one wax having a melting temperature below 70° C. and one wax having a melting temperature from 70° C. to 110° C.

The wax or mixture of waxes introduced in the cosmetic composition according to the invention should be liquid, i.e. should flow under its own weight, in the presence of cetyl phosphate and arginine when heated at a temperature range of above 50° C. to 110° C.

The wax that may be introduced in the cosmetic composition according to the invention can be selected from a polar wax, an apolar wax or mixtures thereof.

The term "polar wax" means a wax comprising at least one heteroatom such as oxygen, nitrogen, silicon or phosphorous.

In particular, the polar wax may be selected from bees wax, candelilla wax, cotton wax, rice bran wax, bayberry wax, Chinese insect wax, montan wax, lanolin, kapok wax, acetylated lanolin, liquid lanolin, sugar cane wax, lanolin fatty acid isopropyl ester, hexyl laurate, reduction lanolin, jojoba wax, hard lanolin, shellac wax, POE lanolin alcohol ether, POE lanolin alcohol acetate, POE cholesterol ether, lanolin fatty acid polyethylene glycol, POE hydrogenated lanolin alcohol ether, and mixtures thereof.

Mention can be also made of the mixture of jojoba esters, polyglycerin-3, acacacia decurrens flower wax and sunflower seed wax, available under trade name Acticire® from GATTEFOSSE.

The term "apolar wax" means a wax consisting solely of carbon and hydrogens atoms and devoid of heteroatoms such as oxygen, nitrogen, silicon or phosphorous.

In particular, the apolar wax may be selected from paraffin wax, polymethylene, polyethylene and/or polypropylene waxes, waxes formed of ethylene/propylene copolymer, micro-crystalline waxes, ozokerite, Fischer-Tropsch waxes, synthetic waxes, and mixtures thereof.

Examples of suitable apolar waxes are sold in particular by Sasol under the trade name Sasol Wax® C80; by Jeen under the trade names Jeenate® 2H to 6H; and by New Phase under the trade names Performalene® 500 and Performa® V343.

Another example of a suitable apolar wax is a mixture of linear polyethylene of high molecular weight and ethylene/propylene copolymer available under trade name Lipwax® PZ80-20 from SAFIC-ALCAN.

According to a particularly preferred embodiment, the structuring agent that is introduced in the composition is a wax is selected from beeswax, candelilla wax, a mixture of linear polyethylene of high molecular weight and ethylene/propylene copolymer, a mixture of jojoba esters, polyglycerin-3, acacacia decurrens flower wax and sunflower seed wax, and mixtures thereof.

When the cosmetic composition of the invention comprises from 4% to less than 8% by weight of water based on the weight of the composition, the cosmetic composition does not comprise a wax selected from carnauba wax, synthetic wax (Sasol wax), polyethylene wax (P400) or ozokerite. Indeed, these waxes are not liquid at a temperature of above 50° C. to 110° C. in the presence of cetyl phosphate and arginine when the composition comprises less than 8% by weight, in particular less than 10% by weight of water.

The oily gellant that may be introduced in the cosmetic composition according to the invention can be selected from a silicone polymer; a cyclic vinyldimethicone/dimethicone copolymer; a polyamide resin or a poly(ester-amide) resin; a copolymer of styrene and at least one olefin other than styrene; an N-acyl glutamic acid diamide; a dextrin ester; a sucroester, and mixtures thereof.

Examples of silicone polymers suitable as oily gellants are organopolysiloxane elastomers. Mention may be made, among these, of the at least partially crosslinked polymers resulting from the reaction of an organopolysiloxane or of a polyether carrying unsaturated groups, such as vinyl or allyl groups, preferably located at the end of the chain, with another reactive silicone compound, such as an organohydropolysiloxane. Examples of such elastomers are sold in particular by Shin Etsu under the trade names KSG 6, KSG 16, KSG 31, KSG 32, KSG 41, KSG 42, KSG 43, KSG 44, KSG-21 and KSG 210; by Dow Corning under the trade names DC 9040 and DC 9041; and by Grant Industries under the trade name Gransil®.

Another example of a silicone polymer suitable as an oily gellant is a silicone polymer obtained by self-polymerization in the presence of a catalyst of an organopolysiloxane functionalized by epoxy groups and hydrosilylated, which is available commercially from General Electric under the trade name Velvesil® 125.

An example of a cyclic vinyldimethicone/dimethicone copolymer suitable as an oily gellant is sold by Jeen under the trade name Jeesilc® PS (including PS VH, PS VHLV, PS CM, PS CMLV and PS DM).

Examples of polyamide resins or poly(ester-amide) resins suitable as oily gellants are ester terminated polyamides (ETPA), ester terminated poly(ester-amides) (ETPEA), tertiary amide terminated polyamides (ATPA), polyalkyleneoxy terminated polyamides (PAOPA) or polyether polyamides (PEPA). Examples of ester terminated polyamides (ETPA) are those identified by INCI name "Ethylenediamine/Stearyl Dimer Dilinoleate Copolymer" and available, for example, under the trade name Uniclear® 100VG from the company Arizona Chemical. Examples of ester terminated poly(ester-amides) (ETPEA) are those identified by INCI name "Bis-stearyl Ethylenediamine/Neopentyl Glycol/Stearyl Hydrogenated Dimer Dilinoleate Copolymer" and available, for example, under the trade name Oleocraft® LP-20-PA-MV from the company Croda (former trade name Sylvaclear® C75V from the company Arizona Chemical). Examples of tertiary amide terminated polyamides (ATPA) are those identified by INCI name "Ethylenediamine/Hydrogenated Dimer Dilinoleate Copolymer Bis-Di-C14-18 Alkyl Amide" and available, for example, under the trade name Sylvaclear® A200V or Sylvaclear® A2614V from the company Arizona Chemical or those identified by INCI name "Diisostearyl malate and bis-dioctadecylamide dimer dilinoleic acid/ethylenediamine" and available, for example, under the trade name Haimalate PAM from the company Kokyu Alcohol Kogyo. Examples of polyalkyleneoxy terminated polyamides (PAOPA) are those identified by the INCI name Polyamide-3 available, for example, under the trade name Sylvaclear® AF1900V, Sylvaclear® PE1800V and Sylvaclear® PA1200V from the company Arizona Chemical. Examples of polyether polyamides (PEPA) are those identified by the INCI name Polyamide-6 available, for example, under the trade name Sylvaclear® PE400V from the company Arizona Chemical.

Examples of copolymers of styrene and at least one olefin other than styrene suitable as an oily gellant are copolymers, in particular block copolymers, of styrene and at least one olefin other than styrene selected from ethylene, propylene, butylene, butadiene, isoprene, and mixtures thereof. Such copolymers are sold by Shell under the trade name Kraton®, and can in particular be a styrene-ethylene-propylene, styrene-ethylene-butylene, styrene-butadiene, styrene-isoprene, styrene-butadiene-styrene, styrene-isoprene-styrene or styrene-ethylene-butylene-styrene copolymer or also an ethylene/propylene/styrene or butylene/ethylene/styrene copolymer or any blend of the abovementioned copolymers, for example a blend of ethylene/propylene/styrene and butylene/ethylene/styrene copolymers. An example of a blend of copolymers which can be used according to the invention is composed of the Dekagel® products sold by Jan Dekker and in particular Dekagel® HV2004. Other examples of styrene copolymers for use in the present invention are those sold by Penreco under the trade names Versagel® M, ME, ML, MP, MC, MD and MN, in particular Versagel® ME, more particularly Versagel® ME 2000.

Examples of N-acyl glutamic acid diamides suitable as an oily gellant are an N-acyl glutamic acid diamide having a straight-chain alkyl group, such as dibutyl lauroyl glutamide, and an N-acyl glutamic acid diamide having a branched-chain alkyl group, such as dibutyl ethylhexanoyl glutamide. Dibutyl lauroyl glutamide is commercially available as GP-1 and dibutyl ethylhexanoyl glutamide is commercially available as EB-21, both from Ajinomoto.

Examples of dextrin esters suitable as an oily gellant are esters of dextrin and fatty acids, such as dextrin palmitate.

Examples of sucrose esters suitable as an oily gellant are esters of sucrose and fatty acids, such as sucrose tetrastearate triacetate available under trade name Sisterna® A10E-C from the company Sisterna.

The cosmetic composition of the invention may, in particular, comprise 1 to 35% by weight, preferably 8 to 30% by weight, of structuring agent based on the weight of the composition.

Oil

The cosmetic composition of the present invention comprises an oil or mixtures thereof.

The term "oil" means a compound which is liquid at ambient temperature (25° C.) and which, when it is introduced in a proportion of at least 1% by weight into water at 25° C., is not at all soluble in water or soluble to a level of less than 10% by weight, with respect to the weight of oil introduced into the water.

In the context of the present invention, the term "oil" also includes lipophilic fats which, like waxes, are capable of undergoing a reversible liquid/solid state change and have an anisotropic crystalline organization in the solid state, but which are different from waxes by the fact that they contain, at a temperature of 23° C., a liquid fraction and a slurry fraction. A compound of this type is notably a mixture of esters of sterols, such as the mixture of cholesterol and lanosterol esters available from CRODA under the trade name Super Sterol Ester®.

The oils which can be used in the composition according to the invention can be chosen from: hydrocarbon oils; synthetic (poly)esters and (poly)ethers, in particular (poly)esters of C6-C20 acids and of C6-C20 alcohols which are advantageously branched, such as isononyl isononanoate; vegetable oils; branched and/or unsaturated fatty acids; branched and/or unsaturated fatty alcohols, such as octyldodecanol; silicone oils, such as linear polydimethylsiloxanes, which are optionally phenylated, or cyclic polydimethylsiloxanes; fluorosilicone oils; fluorinated oils; and their mixtures.

When the cosmetic composition of the invention is a lip balm, it advantageously comprises at least one glossy oil, that is to say an oil exhibiting a refractive index of greater than 1.45 and preferably of greater than 1.47.

Examples of glossy oils are in particular hydrocarbon oils, such as squalane, polybutene, hydrogenated polyisobutene or hydrogenated polydecene, and also phenylated silicone oils, such as those identified by the INCI name "phenyl trimethicone", an example of which is composed of the silicone available under the trade name Mirasil® PTM from Rhodia, those identified by the INCI name "phenylpropyldimethylsiloxysilicate", an example of which is composed of the silicone available under the trade name Silshine® 151 from General Electric, and those identified by the INCI name "trimethyl pentaphenyl trisiloxane", an example of which is composed of the silicone available under the trade name DC PH® 1555 HRI from Dow Corning.

Mention may also be made, as glossy oils, of the fluorinated silicones identified by the INCI name "perfluorononyl dimethicone", an example of which is composed of the silicone available under the trade name Pecosil® FS (FSU, FSL, and the like) from Phoenix and another example of which is composed of the silicone available under the trade name Biosil Basics® (Fluorosil LF, 14, and the like) from Biosil Technologies.

Mention may also be made, as glossy oils, of amino ceramides, such as those identified by the INCI name "phytosteryl/octyldodecyl lauroyl glutamate", available under the trade name Eldew® PS203 from AJINOMOTO.

Other examples of glossy oils are natural oils and in particular castor seed oil; mono- and polyesters of fatty acids and/or of fatty alcohols, the fatty chain of which includes from 6 to 20 carbon atoms, in particular: mono- and polyesters of hydroxy acids and of fatty alcohols, such as diisostearyl malate, esters of benzoic acid and of fatty alcohols, such as C12-C15 alkyl benzoate, polyesters of polyols and in particular of (di)pentaerythritol, such as pentaerythrityl tetraisostearate, dipentaerythrityl pentaisononanoate and dipentaerythrityl C5-C9 esters, or of polyglycerol, such as that known under the INCI name "bis-diglyceryl polyacyladipate-1" and sold by Sasol under the trade name Softisan® 645 or polyglyceryl-2 triisostearate sold by under the Trade name Salacos® 43N by Nisshin OilliO Group Ltd, or of trimethylolpropane, such as trimethylolpropane triethylhexanoate, which is sold in particular by Kokyu Alcohol Kogyo under the trade name Kak® TTO, or of propylene glycol, such as propylene glycol dibenzoate, which is sold in particular by Inolex under the trade name Lexfeel Shine®, and isocetyl stearoyl stearate; and polyesters of hydrogenated castor oil, such as the esters sold by Kokyu Alcohol Kogyo under the trade names Risocast® DA-H and Risocast® DA-L.

The oil used in the cosmetic composition of the invention may also be a non-glossy oil.

Examples of suitable non-glossy oils include volatile linear alcanes such as those described in document FR2933865 which is hereby incorporated by reference. Examples of suitable volatile linear alcanes are C9-C17, in particular C10-C14 alcanes, such as a mixture of undecane and tridecane, available under the trade name Cetiol® Ultimate from BASF Care Creations or C15-19 alcanes available under the trade name Emogreen® L15 from SEPPIC, or C12-14 alcanes available under the trade name Vegelight® 1214LC from Biosynthis; synthetic (poly)esters and (poly)ethers and in particular (poly)esters of C6-C20 acids and of C6-C20 alcohols, advantageously branched, such as isononyl isononanoate and isostearyl neopentanoate; di(C6-C20 alkyl) carbonates such as dicaprylyl carbonate; branched and/or unsaturated fatty acids; silicone oils such as linear polydimethylsiloxanes; and mixtures thereof.

It is clearly understood that the composition according to the invention can comprise mixtures of the oils mentioned above.

According to a preferred embodiment, the oil is selected from hydrocarbon oils; C9-C17 linear volatile alcanes; synthetic (poly)esters and (poly)ethers, in particular (poly)esters of C6-C20 acids and of C6-C20 alcohols which are advantageously branched, such as isononyl isononanoate; vegetable oils; branched and/or unsaturated fatty acids; branched and/or unsaturated fatty alcohols, such as octyldodecanol; and their mixtures.

According to a particularly preferred embodiment, the oil is selected from squalane, diisostearyl malate, a mixture of cholesterol and lanosterol esters, phytosteryl/octyldodecyl lauroyl glutamate, hydrogenated polyisobutene, dicaprylyl carbonate, a mixture of undecane and tridecane, isononyl isononanoate, and mixtures thereof.

The cosmetic composition of the invention can, in particular, comprise 20 to 80% by weight, preferably 30 to 70% by weight, of oil based on the weight of the composition.

Additives

The cosmetic composition of the invention may further comprise an additive selected from a filler, a coloring material, a sweetening agent, a sequestering agent, a pH adjuster, a preservative, a fragrance, a UV screening agent, an antioxidant, and mixtures thereof.

The composition of the invention can include a filler. This term is understood to mean any inorganic or organic particle of any shape (in particular spherical or lamellar) which is insoluble in the composition. Examples of fillers are talc, mica, silica, kaolin, boron nitride, lauroyl lysine, cellulose beads, glass beads, starch, starch modified by octenylsuccinic anhydride, polyamides, silicone resins such as polymethylsilsesquioxane available under the trade name Tospearl 2000B from Momentive Performance Materials powders derived from silicone elastomers such as silicon elastomer coated with silicon resin available under the trade name KSP100 or KSP300 from ShinEtsu and powders derived from acrylic polymers, in particular from poly(methyl methacrylate). The fillers can in particular be composed of several layers of different chemical nature and/or of different physical form and can in particular be provided in the form of lamellae coated with spherical fillers. They can be modified using various surface treatments.

According to a preferred embodiment, the filler is selected from talc, mica, silica, kaolin, boron nitride, lauroyl lysine, cellulose beads, glass beads, starch, starch modified by octenylsuccinic anhydride, silicone resins such as polymethylsilsesquioxane available under the trade name Tospearl 2000B from Momentive Performance Materials powders derived from silicone elastomers such as silicon elastomer coated with silicon resin available under the trade name KSP100 or KSP300 from ShinEtsu.

The composition can also comprise at least one coloring material chosen from water-soluble or fat-soluble dyes, fillers having the effect of coloring and/or opacifying the composition and/or of coloring the lips, such as pigments, pearlescent agents, lakes (water-soluble dyes adsorbed on an inert inorganic carrier), and their mixtures. These coloring materials can optionally be treated at the surface with a hydrophobic agent, such as silanes, silicones, fatty acid soaps, C9-C15 fluoroalkyl phosphates, acrylate/dimethicone copolymers, mixed C9-C15 fluoroalkyl phosphate/silicone copolymers, lecithins, carnauba wax, polyethylene, chitosan and optionally acylated amino acids, such as lauroyl lysine, disodium stearoyl glutamate and aluminum acyl glutamate. The pigments can be inorganic or organic and natural or synthetic. Examples of pigments are in particular iron, titanium or zinc oxides, and also composite pigments and goniochromatic, pearlescent, interference, photochromic or thermochromic pigments, without this list being limiting. Suitable organic pigments that can be used in the composition of the invention include carbon black; pigments of D&C type; lakes based on cochineal carmine, barium, strontium, calcium or aluminium; or alternatively diketopyrrolopyrroles (DPP) such as those described in documents EP-A-542669, EP-A-787730, EP-A-787731 and WO-A-96/08537. The pearlescent agents can be chosen from those conventionally present in makeup products, such as mica/titanium dioxide products. In an alternative form, they can be pearlescent agents based on mica/silica/titanium dioxide, based on synthetic fluorphlogopite/titanium dioxide (Sunshine® from Maprecos), based on calcium sodium borosilicate/titanium dioxide (Reflecks® from Engelhard) or based on calcium aluminum borosilicate/silica/titanium dioxide (Ronastar® from Merck).

Advantageously, when it includes one or more pigments, the composition according to the invention additionally comprises at least one dispersant, such as diisostearyl malate, pentaerythrityl adipate, pentaerythrityl caprate, pentaerythrityl caprylate or pentaerythrityl heptanoate.

When the composition of the invention is a lip balm, it can also include a sweetening agent, such as sorbitol, sucrose, xylitol, acesulfame-K and sodium saccharinate.

The composition of the invention can also include a sequestering agent, such as EDTA salts.

The composition of the invention can in addition comprise at least one UV screening agent chosen from organic and inorganic screening agents and their mixtures. Mention may in particular be made, as organic screening agents, of dibenzoylmethane derivatives (including butyl methoxydibenzoylmethane), cinnamic acid derivatives (including ethylhexyl methoxycinnamate), salicylates, para-aminobenzoic acids, $\beta,\beta$-diphenylacrylates, benzophenones, benzylidene-camphor derivatives, phenylbenzimidazoles, triazines, phenylbenzotriazoles and anthranilic derivatives. Mention may in particular be made, as inorganic screening agents, of screening agents based on inorganic oxides in the form of pigments or nanopigments which may or may not be coated and in particular based on titanium dioxide or on zinc oxide.

The composition of the invention can also include an antioxidant, such as ascorbic acid and/or its alkyl or phosphoryl esters, or also tocopherol and its esters.

Examples of such additives are mentioned in particular in the CTFA dictionary (International Cosmetic Ingredient Dictionary and Handbook published by The Cosmetic, Toiletry and Fragrance Association, $9^{th}$ Edition, 2002).

Cosmetic Composition and Cosmetic Method

Preferably, the composition of the invention is used as product for caring for or making up the lips or the skin, for example a lipstick, a lip balm, a foundation or a concealer.

Another object of the present invention is thus a cosmetic method for caring for or making up the lips or the skin, comprising the topical application to the lips or the skin of the composition as described above.

Cosmetic Article

The cosmetic composition of the invention may be included in a cosmetic article for the lips or the skin.

The cosmetic article for the lips or the skin comprises:
- a container intended to contain a reserve of cosmetic composition;
- at least two grids, said grids exhibiting through-holes and being disposed such that the cosmetic composition sequentially passes through each grid as it dispensed from the container.

When the cosmetic composition has a solid texture, the grids of the cosmetic article make the product pasty which improves the resulting makeup effect and simplifies the application of the makeup for the user.

When the cosmetic composition has a pasty texture, the grids of the cosmetic article make the product fluid which improves the resulting makeup effect and simplifies the application of the makeup for the user.

Advantageously, the lamellar phases, in particular the alpha gels, are still present in the cosmetic composition after it has been dispensed from the cosmetic article.

BRIEF DESCRIPTION OF THE DRAWINGS

The invention will be described in connected with the included drawings, in which.

DESCRIPTION OF THE PREFERRED EMBODIMENTS

The invention will now be illustrated by the following non-limiting examples.

EXAMPLE 1

Lip Balm According to the Invention

A lip balm comprising the following ingredients (amounts expressed as percentages by weight based on the weight of the composition) was prepared:

| REF. | INCI | TRADE NAME | AMOUNT |
|---|---|---|---|
| 101 | CETYL PHOSPHATE | NIKKOL PUREPHOS ALPHA | 1.5 |
| 102 | GLYCERIN | GLYCERINE 4811 | 10.0 |
| 201 | AQUA (WATER) | EAU DEMINERALISEE | 10.0 |
| 202 | ARGININE | L-ARGININE | 0.75 |
| 203 | PHENOXYETHANOL | SEPICIDE LD | 0.40 |
| 301 | SQUALANE | NIKKOL OLIVE SQUALANE | 14.5 |
| 302 | DIISOSTEARYL MALATE | SALACOS 222 | 24.5 |
| 303 | C10-30 CHOLESTEROL/LANOSTEROL ESTERS & TOCOPHEROL | SUPER STEROL ESTER-SO | 18.35 |
| 304 | SYNTHETIC WAX & ETHYLENE/PROPYLENE COPOLYMER | LIPWAX PZ80-20 | 5.0 |
| 305 | CERA ALBA (BEESWAX) | CERABEIL BLANCHE | 5.0 |
| 306 | PHYTOSTERYL/OCTYLDODECYL LAUROYL GLUTAMATE | ELDEW PS-203 | 10.0 |

The process of preparation of the lip balm is detailed below:

- heat 101 and 102 at 75-80° C. with mixing at 100 rpm to form phase (1),
- heat 201, 202 and 203 at 75-80° C. to form phase (2),
- add (2) in (1) in a Deflo disperser (RAYNERI TURBOTEST 33/300P),
- heat 301, 302, 303, 304 and 305 at 105° C. to form phase (3),
- add (3) in (1+2) in small portions with mixing at 500 rpm until a uniform gel is obtained (approximately 10 min), increase the mixing speed to 700 rpm and mix for 5 min.

EXAMPLE 2

Foundation According to the Invention

A foundation comprising the following ingredients (amounts expressed as percentages by weight based on the weight of the composition) was prepared:

| REF. | INCI | TRADE NAME | AMOUNT |
|---|---|---|---|
| 101 | CETYL PHOSPHATE | NIKKOL PUREPHOS ALPHA | 1.5 |
| 102 | GLYCERIN | GLYCERINE 4811 | 10.0 |
| 201 | AQUA (WATER) | EAU DEMINERALISEE | 10.0 |
| 202 | ARGININE | L-ARGININE | 0.75 |
| 203 | PHENOXYETHANOL | SEPICIDE LD | 0.40 |
| 301 | DICAPRYLYL CARBONATE | CETIOL CC | 17.14 |
| 302 | CANDELILLA CERA (*EUPHORBIA CERIFERA* (CANDELILLA) WAX) & BENZYL ALCOHOL | CANDELILLA WAX CG-7 | 8.0 |
| 303 | JOJOBA ESTERS & POLYGLYCERIN-3 & *ACACIA DECURRENS* FLOWER WAX & *HELIANTHUS ANNUUS* CERA SEED (*HELIANTHUS ANNUUS* (SUNFLOWER) SEED WAX) | ACTICIRE | 8.0 |
| 305 | CERA ALBA (BEESWAX) | CERABEIL BLANCHE | 4.0 |
| 306 | SUCROSE TETRASTEARATE TRIACETATE | SISTERNA A10E-C | 2.0 |
| 307 | BORON NITRIDE | BORONEIGE 901 | 1.0 |
| 308 | ETHYLHEXYL METHOXYCINNAMATE & BHT | PARSOL MCX | 5.0 |
| 401 | SQUALANE | NEOSSANCE SQUALANE | 6.14 |
| 402 | CI 77891 (TITANIUM DIOXIDE) & ALUMINUM HYDROXIDE & SODIUM LAUROYL GLUTAMATE & LYSINE & MAGNESIUM CHLORIDE | ASL-1 TIO2 CR-50 | 7.735 |
| 403 | CI 77499 (IRON OXIDES) & SODIUM LAUROYL GLUTAMATE & LYSINE & MAGNESIUM CHLORIDE | ASL-1 BLACK BL-100P | 0.325 |

| REF. | INCI | TRADE NAME | AMOUNT |
|---|---|---|---|
| 404 | CI 77492 (IRON OXIDES) & SODIUM LAUROYL GLUTAMATE & LYSINE & MAGNESIUM CHLORIDE | ASL-1 YELLOW LL-100P | 1.885 |
| 405 | CI 77491 (IRON OXIDES) & SODIUM LAUROYL GLUTAMATE & LYSINE & MAGNESIUM CHLORIDE | ASL-1 RED R-516P | 0.455 |
| 406 | TITANIUM DIOXIDE & STEARIC ACID & ALUMINA & SILICA | UV-TITAN M160 | 7.0 |
| 407 | ZINC OXIDE & TRIETHOXYCAPRYLYLSILANE | OTS-5 MZ-500 | 2.0 |
| 408 | DICAPRYLYL CARBONATE | CETIOL CC | 6.67 |

The process of preparation of the foundation is detailed below:
- heat 101 and 102 at 75-80° C. with mixing at 100 rpm to form phase (1),
- heat 201, 202 and 203 at 75-80° C. to form phase (2),
- add (2) in (1) in a Deflo disperser (RAYNERI TURBOTEST 33/300P),
- mill 401, 402, 403, 404, 405, 406, 407 and 408 in a tricylinder to form phase (4),
- heat (4) and 301, 302, 303, 304, 305, 306, 307 and 308 at 95° C. to form phase (4+3),
- add (4+3) in (1+2) in small portions with mixing at 500 rpm until a uniform gel is obtained (approximately 10 min),
- increase the mixing speed to 700 rpm and mix for 5 min, degas under vacuum,
- pour in container at 85° C.,
- leave at room temperature for 2 min then put in ventilated freezer at −10° C. for 2 min.

EXAMPLE 3

Concealer According to the Invention

A concealer comprising the following ingredients (amounts expressed as percentages by weight based on the weight of the composition) was prepared:

| REF. | INCI | TRADE NAME | AMOUNT |
|---|---|---|---|
| 101 | CETYL PHOSPHATE | NIKKOL PUREPHOS ALPHA | 1.5 |
| 102 | GLYCERIN | GLYCERINE 4811 | 10.0 |
| 201 | AQUA (WATER) | EAU DEMINERALISEE | 10.0 |
| 202 | ARGININE | L-ARGININE | 0.75 |
| 203 | PHENOXYETHANOL | SEPICIDE LD | 0.40 |
| 301 | DICAPRYLYL CARBONATE | CETIOL CC | 17.14 |
| 302 | CANDELILLA CERA (*EUPHORBIA CERIFERA* (CANDELILLA) WAX) & BENZYL ALCOHOL | CANDELILLA WAX CG-7 | 8.0 |
| 303 | JOJOBA ESTERS & POLYGLYCERIN-3 & *ACACIA DECURRENS* FLOWER WAX & *HELIANTHUS ANNUUS* CERA SEED (*HELIANTHUS ANNUUS* (SUNFLOWER) SEED WAX) | ACTICIRE | 8.0 |
| 305 | CERA ALBA (BEESWAX) | CERABEIL BLANCHE | 4.0 |
| 306 | SUCROSE TETRASTEARATE TRIACETATE | SISTERNA A10E-C | 2.0 |
| 307 | BORON NITRIDE | BORONEIGE 901 | 1.0 |
| 308 | ETHYLHEXYL METHOXYCINNAMATE & BHT | PARSOL MCX | 5.0 |
| 401 | SQUALANE | NEOSSANCE SQUALANE | 6.14 |
| 402 | CI 77891 (TITANIUM DIOXIDE) & ALUMINUM HYDROXIDE & SODIUM LAUROYL GLUTAMATE & LYSINE & MAGNESIUM CHLORIDE | ASL-1 TIO2 CR-50 | 7.735 |
| 403 | CI 77742 (MANGANESE VIOLET) | MANGANESE VIOLET C 43-001 | 2.665 |
| 404 | TITANIUM DIOXIDE & STEARIC ACID & ALUMINA & SILICA | UV-TITAN M160 | 7.0 |
| 405 | ZINC OXIDE & TRIETHOXYCAPRYLYLSILANE | OTS-5 MZ-500 | 2.0 |
| 406 | DICAPRYLYL CARBONATE | CETIOL CC | 6.67 |

The process of preparation of the concealer is detailed below:
- heat 101 and 102 at 75-80° C. with mixing at 100 rpm to form phase (1),
- heat 201, 202 and 203 at 75-80° C. to form phase (2),
- add (2) in (1) in a Deflo disperser (RAYNERI TURBOTEST 33/300P),
- mill 401, 402, 403, 404, 405 and 406 in a tricylinder to form phase (4),
- heat (4) and 301, 302, 303, 304, 305, 306, 307 and 308 at 90° C. to form phase (4+3),
- add (4+3) in (1+2) in small portions with mixing at 500-600 rpm until a uniform gel is obtained (approximately 10 min).

EXAMPLE 4

Evaluation of the Moisturizing Effect of the Cosmetic Compositions of the Invention The moisturizing effect of the lip balm prepared in example 1 and the foundation prepared in example 2 are determined by corneometry.

Corneometry is a technology used to measure the hydration of the outer layer of the epidermis (stratum corneum). The measurement is based on capacitance measurement of a dielectric medium. The capacitance of the skin is measured with a Corneometer® CM825 apparatus from Courage+Khazaka electronic GmbH. The Corneometer® CM 825 measures the change in the dielectric constant due to skin surface hydration changing the capacitance of a precision capacitor. The measurement can detect even slight changes in the hydration level.

The measurement is performed on the skin of the inside of the forearms of 8 volunteers that have not applied any cream on the forearms at least 24 h before the test.

A control area (no product is applied) of 1.5 cm×3 cm is delineated with a stencil.

A test area where the cosmetic composition is applied of 5 cm×5 cm is delineated with a stencil.

The cosmetic composition to be evaluated is applied on the test area in a single application with a finger glove in an amount of 2 mg/cm², i.e. 0.05 mg of composition on the 5 cm×5 cm test area.

The capacitance of the skin is measured before (T0), 30 min after (T30'), 2 hours after (T2 h) and 6 hours after (T6 h) application of the cosmetic composition.

The difference in corneometric index at time i (30 min, 2 hours and 6 hours after application) is calculated as follows:

$$\Delta ci_i = (Ti-T0)_{test\ area} - (Ti-T0)_{control\ area}$$

wherein:

$\Delta ci_i$ is the difference in corneometric index at time i, $(Ti-T0)_{test\ area}$ is the difference between the average of the capacitance of the test area at time i and the average of the capacitance of the test area at time T0 (before application), $(Ti-T0)_{control\ area}$ is the difference between the average of the capacitance of the control area at time i and the average of the capacitance of the control area at time T0 (before application), and time i is 30 min, 2 hours or 6 hours after application of the cosmetic composition on the test area.

Figure 1:
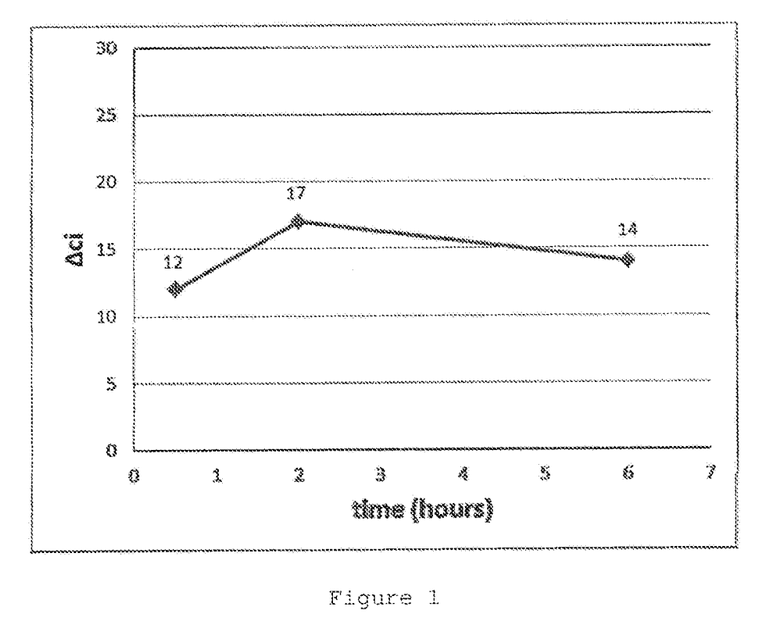
FIG. 1 represents the difference in corneometric index ($\Delta$ci) as a function of time after application of the lip balm prepared in example 1.

FIG. 1 represents the difference in corneometric index ($\Delta ci$) as a function of time after application of the lip balm prepared in example 1.

Figure 2:
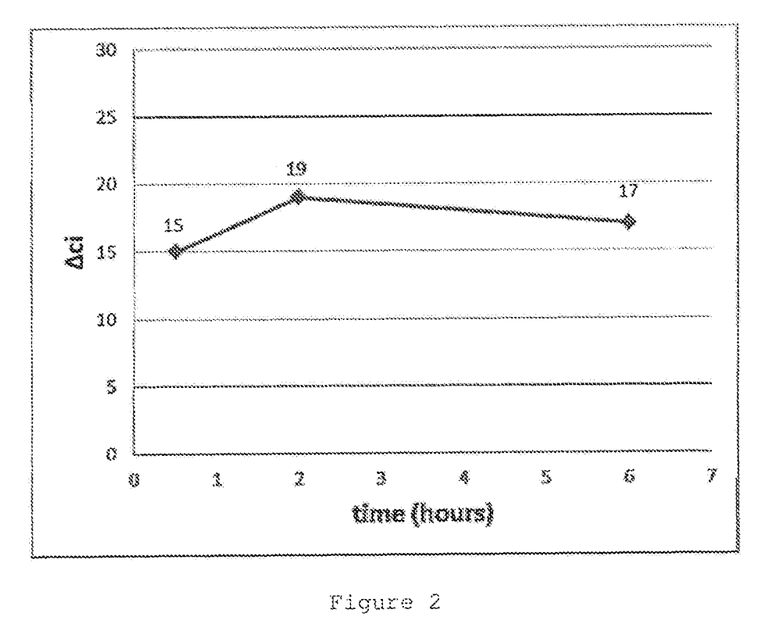
FIG. 2 represents the difference in corneometric index ($\Delta$ci) as a function of time after application of the foundation prepared in example 2.

FIG. 2 represents the difference in corneometric index ($\Delta ci$) as a function of time after application of the foundation prepared in example 2.

The lip balm and the foundation according to the present invention both exhibit an excellent moisturizing effect that lasts up to 6 hours after their application on the skin. Indeed, all of the values of $\Delta ci$ are much higher than 5 which is the threshold limit for determining the moisturizing effect of a cosmetic composition.

The invention claimed is:

1. Cosmetic composition in the form of a solid water-in-oil emulsion comprising:
   - a non-ionic alkyl phosphate;
   - a base;
   - a humectant;
   - 4% to 20% by weight of water based on the weight of the composition;
   - 8 to 30% by weight, relative to the total weight of the composition, of a structuring agent selected from the group consisting of beeswax, candelilla wax, a mixture of ethylene/propylene copolymer and synthetic wax, a mixture of jojoba esters, polyglycerin-3, acacacia decurrens flower wax, sunflower seed wax, an oily gellant, and mixtures thereof;
   - an oil;
   - wherein the composition is liquid when heated at a temperature greater than 50° C. and up to 110° C.

2. Cosmetic composition according to claim 1, comprising at least 8% by weight of water based on the weight of the composition.

3. Cosmetic composition according to claim 1, comprising 0.5 to 5% by weight of a non ionic alkyl phosphate based on the weight of the composition, wherein the non-ionic alkyl phosphate is cetyl phosphate.

4. Cosmetic composition according to claim 3, comprising, 1 to 2.5% by weight, of non-ionic alkyl phosphate based on the weight of the composition.

5. Cosmetic composition according to claim 1, comprising 0.2 to 2.5% by weight of base based on the weight of the composition, wherein the base is a basic amino acid.

6. Cosmetic composition according to claim 5, comprising 0.5 to 1% by weight of base based on the weight of the composition, wherein the base is arginine.

7. Cosmetic composition according to claim 1, comprising 1 to 30% by weight of humectant based on the weight of the composition, wherein the humectant is selected from glycerol, a glycol, and mixtures thereof.

8. Cosmetic composition according to claim 7, comprising, 5 to 20% by weight, of humectant based on the weight of the composition.

9. Cosmetic composition according to claim 8, comprising 8 to 15% by weight, of humectant based on the weight of the composition.

10. Cosmetic composition according to claim 1, comprising up to 30% by weight of water based on the weight of the composition.

11. Cosmetic composition according to claim 1, wherein the structuring agent is a mixture of at least one wax having a melting point below 70° C. and one wax having a melting point from 70° C. to 110° C.

12. Cosmetic composition according to claim 1, comprising 20 to 80% by weight of oil based on the weight of the composition, wherein the oil is selected from squalane, diisostearyl malate, a mixture of cholesterol and lanosterol esters, phytosteryl/octyldodecyl lauroyl glutamate, hydrogenated polyisobutene, dicaprylyl carbonate, a mixture of undecane and tridecane, isononyl isononanoate, and mixtures thereof.

13. Cosmetic method for caring for or making up the lips or the skin, comprising the topical application to the lips or the skin of the composition as claimed in claim 1.

* * * * *